United States Patent
Li et al.

(10) Patent No.: US 10,130,340 B2
(45) Date of Patent: Nov. 20, 2018

(54) METHOD AND APPARATUS FOR NEEDLE VISUALIZATION ENHANCEMENT IN ULTRASOUND IMAGES

(71) Applicant: KONINKLIJKE PHILIPS N.V., Eindhoven (NL)

(72) Inventors: Junbo Li, Shanghai (CN); Jing Ping Xu, Shanghai (CN); Yinan Chen, Shanghai (CN); Yunrong Zhang, Shanghai (CN)

(73) Assignee: Koninklijke Philips N.V., Eindhoven (NL)

( * ) Notice: Subject to any disclaimer, the term of this patent is extended or adjusted under 35 U.S.C. 154(b) by 764 days.

(21) Appl. No.: 14/369,697

(22) PCT Filed: Dec. 14, 2012

(86) PCT No.: PCT/IB2012/057317
§ 371 (c)(1),
(2) Date: Jun. 29, 2014

(87) PCT Pub. No.: WO2013/098696
PCT Pub. Date: Jul. 4, 2013

(65) Prior Publication Data
US 2014/0362114 A1  Dec. 11, 2014

(30) Foreign Application Priority Data
Dec. 30, 2011 (WO) ................ PCT/CN2011/085034

(51) Int. Cl.
*A61B 8/08* (2006.01)
*A61B 8/00* (2006.01)
(Continued)

(52) U.S. Cl.
CPC .......... *A61B 8/5207* (2013.01); *A61B 8/0841* (2013.01); *A61B 8/461* (2013.01);
(Continued)

(58) Field of Classification Search
None
See application file for complete search history.

(56) References Cited

U.S. PATENT DOCUMENTS

| | | | |
|---|---|---|---|
| 2006/0204042 A1* | 9/2006 | Hammoud | A61B 5/1103 382/107 |
| 2010/0104148 A1* | 4/2010 | Bovik | G06K 9/4633 382/128 |
| 2010/0121190 A1 | 5/2010 | Pagoulatos et al. | |
| 2010/0283462 A1 | 11/2010 | Wang et al. | |

(Continued)

FOREIGN PATENT DOCUMENTS

| | | |
|---|---|---|
| WO | WO2007016369 | 2/2007 |
| WO | WO2011137336 | 3/2011 |

OTHER PUBLICATIONS

Perperidis, A. et al. "Temporal compounding and its effect on clinical measurements of cardiac ultrasound data", Conf Proc IEEE Eng Med Biol Soc. 2009;2009:3661-4. doi: 10.1109/IEMBS.2009.5333690.

(Continued)

*Primary Examiner* — Xin Sheng

(57) ABSTRACT

A method and an apparatus or needle visualization enhancement in ultrasound (US) imaging includes a Radon transform (RT) unit configured to perform RT on a sequence of frames to detect line features in the frames, where a frame includes US radio-frequency (RF) data obtained during monitoring the insertion of a needle into a subject or an US image reconstructed from the RF data. Further, a false needle feature removing unit is configured to remove line features which remain substantially stationary among the frames as false needles while locating a line feature which extends among the frames as the needle; and an overlaying unit is configured to overlay the location of the line feature as the needle on an US image of a frame to produce an enhanced image to be displayed.

13 Claims, 2 Drawing Sheets

(51) Int. Cl.
*G06T 5/00* (2006.01)
*G06T 7/254* (2017.01)
*G06T 7/262* (2017.01)

(52) U.S. Cl.
CPC ............ *A61B 8/463* (2013.01); *A61B 8/5215* (2013.01); *A61B 8/5269* (2013.01); *G06T 5/003* (2013.01); *G06T 7/254* (2017.01); *G06T 7/262* (2017.01); *A61B 8/4488* (2013.01); *A61B 8/466* (2013.01); *A61B 8/486* (2013.01); *G06T 2207/10132* (2013.01); *G06T 2207/20048* (2013.01); *G06T 2207/30021* (2013.01)

(56) References Cited

U.S. PATENT DOCUMENTS

2012/0004533 A1* 1/2012 Peng ................. A61B 6/12
600/424
2014/0362114 A1 12/2014 Li et al.

OTHER PUBLICATIONS

Howe, Robert D., "Fixing the Beating Heart: Ultrasound Guidance for Robotic Intracardiac Surgery", Mechanical & Industrial Engineering, University of Toronto, Abstract. Chapter—Functional Imaging and Modeling of the Heart, vol. 5528 of the series Lecture Notes in Computer Science pp. 97-103, 2009.

Neshat, HRS et al., "Real-Time parametric curved needle segmentation in 3D ultrasound images", 2008 2nd IEEE RAS & EMBS International Conference on Biomedical Robotics and Biomechatronics, vol. 1 and 2, pp. 758-763, 2008.

Chen, Cy et al. "Ultrasound image enhancement based on the combination of fuzzy set and radon transform enhancement algorithm for ultrasound image", 2010 3rd International Conference on Advanced Computer Theory and Engineering, Proceedings Jan. 2010; 1. DOI: 10. 1109/ICACTE.2010.5579003.

M. Barva, et al., "Radial Radon Transform Dedicated to Micro-Object Localization from Radio Frequency Ultrasound Signal", 2004 IEEE International Ultrasonics, Ferroelectrics, and Frequency Control Joint 50th Anniversary Conference, 2004, pp. 1836-1839.

P.M. Novotny, et al., "GPU Based Real-Time Instrument Tracking with Three-Dimensional Ultrasound", Science Direct, Medical Image Analysis 11 (2007), pp. 458-464.

Toft, P. et al., The Radon Transform, Theory and Implementation, PhD Thesis, Technical University of Denmark, 1996.

Deans, S., The Radon Transform and some of its applications, John Wiley and Sons, 1983.

* cited by examiner

METHOD AND APPARATUS FOR NEEDLE VISUALIZATION ENHANCEMENT IN ULTRASOUND IMAGES

CROSS-REFERENCE TO PRIOR APPLICATIONS

This application is the U.S. National Phase application under 35 U.S.C. § 371 of International Application Serial No. PCT/IB2012/057317, filed on Dec. 14, 2012, which claims the benefit of International Application Serial No. PCT/CN2011/085034, filed on Dec. 30, 2011. These applications are hereby incorporated by reference herein.

FIELD OF THE INVENTION

The invention relates to ultrasound (US) imaging, and particularly to enhancing the visualization of a needle in an ultrasound image during monitoring the needle moving in a subject.

BACKGROUND OF THE INVENTION

During needle biopsy and some interventional therapy, clinicians need to insert a needle into a subject, such as the body, to reach a target mass. Usually US imaging is used for live monitoring the needle insertion procedure. To deliver a safe and successful procedure, it is critical to locate the needle accurately in the guided US image. Unfortunately, in clinical practice the visibility of the needle in the conventional US image is poor, resulting in difficulty for clinicians to insert the needle accurately.

Different techniques have been used to achieve better needle visualization in US images, for example, adaptively steering the US beam towards the needle to improve the acoustic reflection of the needle and compounding with the non-steered US image; manipulating the needle surface coating, geometry and diameter to enhance acoustic reflection; providing an extra optical or electro-magnetic position sensor on the needle to track the needle location in the US image, etc. In these techniques, either a specially designed needle is used, or an extra position sensor is attached to the needle, or the US imaging system is manipulated to enhance the visualization of the needle. Those approaches will lead to an increase of the total cost of providing enhanced needle visualization.

SUMMARY OF THE INVENTION

The present invention provides a way to improve needle visibility in the US image to be displayed.

According to one aspect of the present invention, there is provided a method of needle visualization enhancement in US imaging, comprising the steps of:

performing a Radon transform (RT) on a sequence of frames to detect line features in the frames, a frame comprising US radio-frequency (RF) data obtained during monitoring the insertion of a needle into a subject or an US image reconstructed from the RF data;

removing line features which remain substantially stationary among the frames as false needles while locating a line feature which extends among the frames as the needle; and overlaying the location of the line feature as the needle on an US image of a frame to produce an enhanced image to be displayed.

Through extracting the location of the needle feature and superimposing it on the US image, the needle visualization presented to the viewer is improved.

According to an embodiment of the present invention, the step of removing line features which remain substantially stationary among the frames as false needles while locating a line feature which extends among the frames as the needle further comprises:

comparing the locations of the detected line features among the frames on a basis of one frame to another; and removing a line feature as false needle if the location difference of the line feature among the frames is below a threshold, and locating a line feature as the needle if the location difference of the line feature among the frames is above the threshold.

According to an embodiment of the present invention, the step of removing line features which remain substantially stationary among the frames as false needles while locating a line feature which extends among the frames as the needle comprises:

determining, for every two consecutive frames of the sequence after the RT, the location difference of each of the detected line features between the two frames, and accumulating the location differences of the line feature to obtain an accumulated location difference of the line feature; and removing a line feature as false needle if the accumulated location difference of the line feature is below a threshold, and locating a line feature as the needle if the accumulated location difference of the line feature is above the threshold.

Through the accumulation of the location differences, the locating of the needle feature and the removing of a false needle feature may be more robust.

According to an embodiment of the present invention, motion compensation may be performed for the sequence of frames before performing RT. The motion compensation may cancel out the effect of potential patient motion artifact on the calculated needle location. The global motion compensation may comprise:

calculating a global motion vector for each of the frames relative to a reference frame; and performing motion compensation for each of the frames using its global motion vector.

According to an embodiment of the present invention, the sequence of frames may be binarized into dark and bright frames before the RT is performed. For example, the values of the pixels in a frame are binarized into "0" or "1" values by thresholding. The threshold may be set as an experimental value, for example, 0.8·Imax, where Imax is the maximum pixel value, or the threshold may be set as the average of values in the frame, or a value resulting from multiplying the average by a factor. The thresholding may facilitate the process of the following RT.

According to an embodiment of the present invention, temporal compounding may be performed for the sequence of frames to produce a compounding frame which has an improved visualization in comparison with each individual frame in the sequence. Then the detected line feature as the needle may be overlaid on the US image of the compounding frame to produce the enhanced image. In this way, the location of the needle as well as the US image may be enhanced in the displayed image.

According to another aspect of the present invention, there is provided an apparatus for needle visualization enhancement in US imaging, comprising:

a Radon transform (RT) unit adapted to perform RT on a sequence of frames to detect line features in the frames, a frame comprising US RF data obtained during monitoring the insertion of a needle into a subject or an US image reconstructed from the RF data;

a false needle feature removing unit adapted to remove line features which remain substantially stationary among the frames as false needles while locating a line feature which extends among the frames as the needle; and an overlaying unit adapted to overlay the location of the line feature as the needle on an US image of a frame to produce an enhanced image to be displayed.

According to another aspect of the present invention, there is provided an US imaging system, comprising an US transducer array adapted to pick up an US RF signal;

an image processor adapted to perform a Radon transform (RT) on a sequence of frames to detect line features in the frames, a frame comprising US RF data obtained during monitoring the insertion of a needle into a subject or an US image reconstructed from the RF data, and remove line features which remain substantially stationary among the frames as false needles while locating a line feature which extends among the frames as the needle; and overlay the location of the line feature as the needle on a US image of a frame to produce an enhanced image to be displayed; and a display adapted to display the enhanced image.

Other objects and advantages of the present invention will become more apparent and will be easily understood from the description made in combination with the accompanying drawings.

DESCRIPTION OF THE DRAWINGS

The present invention will be described and explained hereinafter in more detail in combination with embodiments and with reference to the drawings, wherein.

The same reference signs in the figures indicate similar or corresponding features and/or functionalities.

DETAILED DESCRIPTION

The embodiment of the present invention will be described hereinafter in more detail with reference to the drawings.

Figure 1:
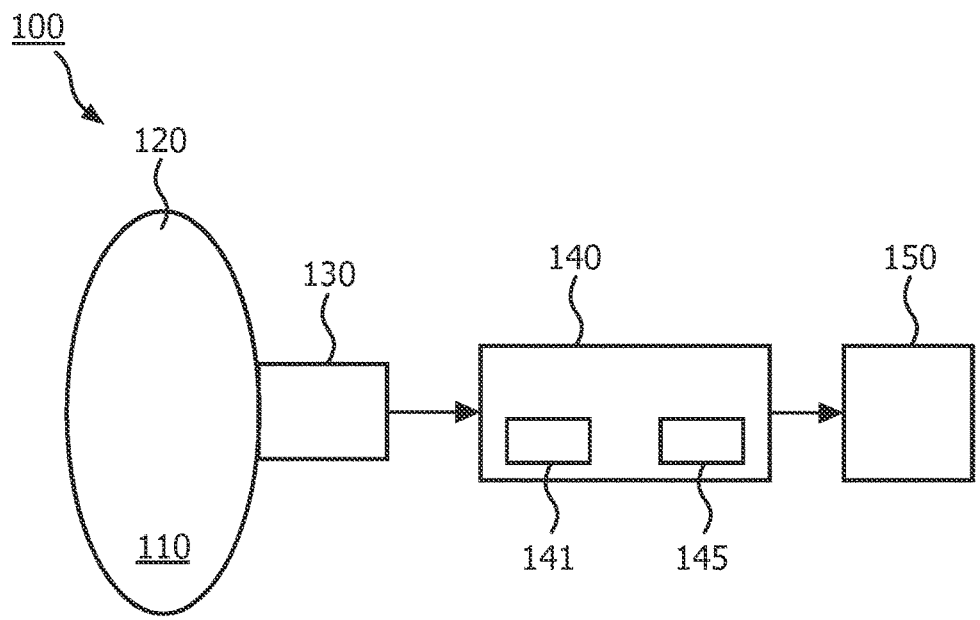
FIG. 1 is a schematic diagram of an US system for monitoring the position of a needle moving in a subject in accordance with an embodiment of the present invention.

FIG. 1 shows a schematic diagram of an US system 100 for monitoring the location of a needle 120 moving in a region of a subject 110 in accordance with an embodiment of the present invention. The subject 110 may be a human being, animals or inanimate objects. The needle 120 may be termed differently in accordance with other terminologies, which refer to it as a line-segment shape instrument, for which the present invention is applicable.

The US system 100 is configured to produce images of the region of the subject 110 during the guiding of the needle insertion into the subject. As shown in FIG. 1, the US system 100 includes an US transducer 130, an imaging processor 140 and a display 150. The US transducer 130 may be an array of transducers for transmitting US signals into a region of the subject 110 and/or receiving corresponding reflected US signals in response to the transmitted US signals. The transducer 130 can convert the reflected US signals to electrical signals, which present the US radio frequency (RF) signal, and transmit the electrical signals to the imaging processor 130. The imaging processor 130 may (e.g., with appropriate software and/or electronics) determine a subject image (e.g., intensities of pixels for an image) and transmit the image to a display 150 for displaying the image.

The imaging processor may include an image reconstruction module 141 and an enhancement module 145. According to an embodiment of the present invention, the US system 100 may work in a conventional way initially, in which the image reconstruction module 141 reconstructs US images, such as conventional B-mode US images, in a conventional way while the enhancement module is not activated. The enhancement module may be activated by an operator at any time. For example, before inserting the needle 120 into the subject 110, the operator such as a clinician may trigger a needle enhancement mode, so that the enhancement module 145 is activated to provide enhanced images. Of course, the enhancement module 145 may be activated automatically when the system 100 turns on.

Figure 2:
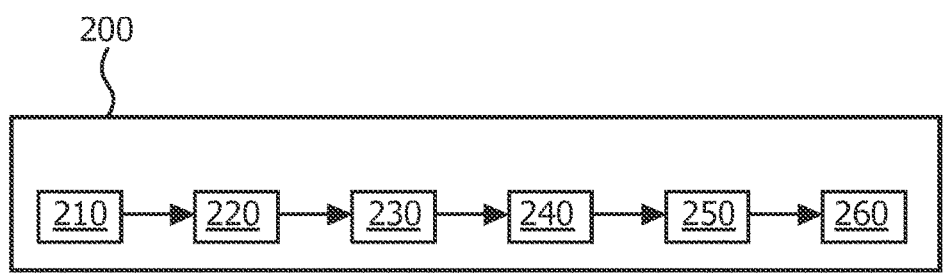
FIG. 2 is a block diagram of an enhancement module for producing an enhanced image in which needle visualization is enhanced in an US image in accordance with an embodiment of the present invention.

FIG. 2 is a block diagram of enhancement module 200 for producing an enhanced image in which needle visualization is enhanced in an US image in accordance with an embodiment of the present invention. The enhancement module 200 may be the enhancement module 145 as shown in FIG. 1. The enhancement module 200 may process a sequence of US images, which are reconstructed by the reconstruction module 141 from US RF data collected by the transducer 130, to produce an enhanced image. The enhancement module 200 may also directly process a sequence of US RF data collected by the transducer 130 in order to produce the enhanced image. For sake of illustration, the sequence of US images or the sequence of US RF data may be collectively referred to as a sequence of frames. And the sequence of frames may present a two-dimensional (2D)/three-dimensional (3D) US image sequence or a 2D/3D US RF sequence.

As shown in FIG. 2, the enhancement module 200 may include a motion compensation unit 210, a thresholding unit 220, a Radon transformation (RT) unit 230, a false needle feature removing unit 240, a temporal compounding unit 250, an overlaying unit 260.

The motion compensation unit 210 is adapted to perform global motion compensation for the sequence of frames.

The thresholding unit 220 is adapted to binarize the frames into dark and bright frames by thresholding.

The RT unit 230 is adapted to perform RT on the sequence of frames to detect line features in the frames.

The false needle feature removing unit 240 is adapted to remove line features which remain substantially stationary among the sequence of frames as false needles while locating a line feature which extends among the sequence of frames as the needle.

The temporal compounding unit 250 is adapted to perform temporal compounding on the sequence of frames to produce a compounding frame.

The overlaying unit 260 is adapted to overlay the location of the line feature as the needle on the US image of a frame to produce an enhanced image to be displayed. The frame on which the line feature is overlaid may be the compounding frame, or any one of the sequence of frames, for example, the last one of the sequence of frames.

It should be understood that the modules as shown in FIG. 1 and the units as shown in FIG. 2 may be implemented in a processor, for example, the imaging processor 140, or may be implemented in several hardware components, for example, the image reconstruction module may be implemented in a dedicated processing unit such as a Digital Signal Processor (DSP) or an Application Specific Integrated Circuit (ASIC) or the like designed specifically for US image reconstructions, and the enhancement module or the units therein may be implemented in a general purpose processor, controller or the like.

It should be understood that the modules as shown in FIG. 1 and the units as shown in FIG. 2 may be implemented in software as computer program product, the functions of the modules and/or units may be stored on or transmitted as program instructions or codes on a computer-readable medium. Computer-readable media are to be taken to include any medium that facilitates transfer of a computer program from one place to another and that can be accessed by a computer. By way of example, the computer-readable media may include RAM, ROM, EEPROM, CD-ROM or other optical disk storage, magnetic disk storage or other magnetic storage devices, or any other medium that can be used to carry or store a desired program code in the form of instructions or data structures and that can be accessed by a computer.

Figure 3:
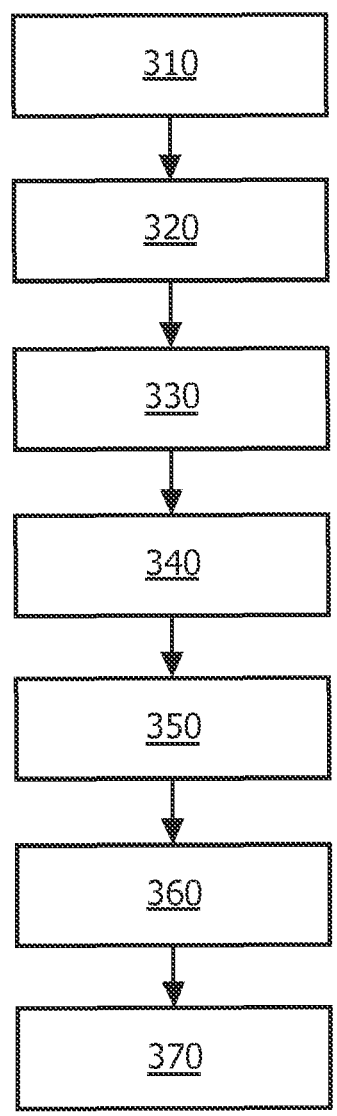
FIG. 3 is a flowchart of the method for producing an enhanced image in which needle visualization is enhanced in an US image in accordance with an embodiment of the present invention.

FIG. 3 is a flowchart of the method 300 of producing an enhanced image in which needle visualization is enhanced in an US image in accordance with an embodiment of the present invention. Next, the method will be described in connection with the illustrated system or apparatus as shown in FIGS. 1 and 2.

The method starts by receiving a sequence of frames by the enhancement module at step 310. For sake of explanation, we may assume the sequence to include n frames, that is, frame 1 to frame n, from which an enhanced frame will be produced in the enhancement module. For example, the next sequence may include frame 2 to frame n+1, the further next sequence may include frame 3 to frame n+2, and so on. Therefore, the enhancement module 200 would supply continually enhanced frames.

Motion compensation may be performed for the received frames, for example frames 1 to n, by the motion compensation unit 210 (step 320). The motion compensation unit 210 may calculate a global motion vector for each of the frames relative to a reference frame, and perform motion compensation for each of the frames, using its global motion vector. The reference frame may be selected as one of the received frames, for example, the first one of the sequence of frames. Said global motion compensation may be performed for every received frame to cancel out potential patient motion, which may lead to artifacts in the finally calculated needle location. The motion compensation step is preferably performed in a preferred embodiment of the present invention. But it is not an inevitable step for the implementation of the present invention, for example, when the subject remains substantially stationary during the procedure of needle insertion.

The sequence of frames may be binarized into dark and bright frames by, for example, the thresholding unit 220 (step 330). For example, the values of the pixels in a frame may be binarized to a first or a second value, which for example may be 0 or 1, 0 or 255, or some other values. The threshold may be set as an experimental value, for example, 0.8 Imax, where Imax is the maximum pixel value, or the threshold may be set as the average of the pixel values in the frame, or a value resulting from multiplying the average by a factor. The sequence of frames resulting from the thresholding step may facilitate reducing the computation load of the RT to be performed. But those skilled in the art should understand that the RT may be performed for the sequence of frames without the thresholding step performed beforehand.

RT may be performed on the sequence of frames, after the thresholding step, by for example the RT unit 230 (step 340). The RT is a linear transformation that has a property of allowing to detect line features in image data. The details for RT are available in the prior art, for example, reference may be made to Toft P., The Radon Transform, Theory and Implementation, PhD Thesis, Technical University of Denmark, p. 23-80; Dean S., The Radon Transform and Some of its Applications, John Wiley and Sons: New York. An adaptive RT may be performed on a frame to detect the line features of the frame. At the same time, the RT has the function of removing artifacts like comet-tail. After applying RT to a frame, the projection angles and vector parameters of the frame will be obtained. The line features will be shown in the Radon transformed frame as peaks (i.e., local maximum), with projection angles representing the angles of the line features in the frame and projection vectors representing the smallest distances of the line features to the projection original. By detecting the local peaks in the RT, line features of the frame can be detected. The location of a line feature is determined by the projection angle and vector of the corresponding peak. For sake of description, we may refer to the projection angle and vector obtained in RT as location information of the line feature.

The needle may curve during the insertion into the subject. In order to ensure that the curved needle is detected, the RT tolerance may be set to a larger value to track line features with small curvature. In addition to line features resulting from the needle, other line features in the frame may also be detected by the RT, which latter line features may be referred to as false needle features. The larger the tolerance that the RT provides, the more line features may be detected by the RT. According to an embodiment of the present invention, the RT is performed on every frame of the sequence. Other variants of the embodiment may be anticipated, for example, the RT may be performed on any two or more frames of the sequence in order to detect the line feature of the needle.

Removing false needle features may be performed on the sequence of frames after RT (step 350) by for example the false needle feature removing unit 240. As stated above, the RT may produce multiple line features. The inventors of the present invention carefully studied the property of the line features and realize that the false needle features remain substantially stationary among adjacent frames while the needle feature extends in adjacent images during the insertion procedure. Therefore, in step 350, the false needle feature removing unit 240 removes line features which remain substantially stationary among the frames as false needles, and locates a line feature which extends among the frames as the needle.

According to an embodiment of the present invention, in step 350, the false needle feature removing unit 240 may compare the locations of the detected line features of any two or more frames of the sequence on a basis of one frame to another. For example, the false needle feature removing unit 240 may compare the locations of the detected line features of a frame to the locations of the detected line features of another frame, and identify a line feature as a false needle that is to be removed if the location difference of the line feature between the two frames is negligible, in other words, the location difference is below a threshold, and identify a line feature as the needle that is to remain if the location difference of the line feature between the two frames is above the threshold. In another example, the false needle feature removing unit 240 may compare the location differences of the line features of the frame and identify a line feature having the largest location difference as the needle that is to remain. As stated above, the projection angle and projection vector of a peak obtained in RT is the location information of the line feature corresponding to the peak. And the location difference of a line feature may be obtained by comparing the projection angle and projection vector of a peak corresponding to the line feature in a frame with that corresponding to the line feature in another frame.

According to an embodiment of the present invention, since the needle can only be inserted in a certain direction, the false needle feature removing unit 240 may only consider line features with projection angles in a certain range (for example 20-70 degrees and 110-170 degrees) as the possible needle, and remove the line features with projection angles outside this range directly as false features.

After applying RT to the sequence of frames 1 to n, the location information of the line features, that is, projection angles and vector parameters of the peaks of the line features in the frame, is detected. During needle insertion, the projection angles of the line feature resulting from the needle will not change much over time, while the projection vector will increase. Comparing the projection angles and vectors of the sequence of images 1 to n, the line features following such a pattern will be regarded as the needle. For example, the false needle feature removing unit 240 may determine the location difference of a line feature between each two consecutive frames of the sequence, and accumulate the resulted location differences of the line feature to obtain an accumulated location difference of the line feature. For example, the false needle feature removing unit 240 may determine the location difference of a line feature between frame 1 and frame 2, between frame 2 and frame 3, . . . , between frame n-1 and frame n, and accumulate the resulting location differences to achieve the accumulated location difference of the line feature in the sequence. As stated above, by comparing the accumulated location differences of the line features with a threshold or with each other, the line feature of the needle may be located and the line feature of a false needle may be removed. After the corresponding projection angle and vector of the needle feature are identified, the location of the needle feature in the US image will be also defined from the projection angle and vector.

According to an embodiment of the present invention, the introduction of outliers due to image distortion may also be considered, i.e., one sudden rise in location information such as project angle and/or vector of a local maximum in the RT may be regarded as an outlier and may not be considered as the needle feature.

According to an embodiment of the present invention, the projection angle of the needle from the previous frame may be used as an initial to search for the needle feature in the next sequence of frames 2 to n+1, for example, only line features with a projection angle in the range of +-10 degrees relative to the previous projection angle of the needle feature may be considered as the possible needle feature. In an example, the RT may be performed in such a range of angles.

It is possible that the needle remains substantially stationary in the sequence of images. In such a case, the line feature of the needle will be removed along with the line features of the false needle in the false needle feature removing step 350, in other words, no line feature is located as the needle. According to an embodiment of the present invention, the false needle feature removing unit 240 may determine that the needle remains substantially stationary at the current time, and may take the previously determined line feature of the needle as the current one.

A temporal compounding process may be performed on the sequence of frames 1 to n by, for example, the temporal compounding unit 250 (step 360) to produce a compounding frame which has an improved visualization as compared to each individual frame in the sequence. In an example, the temporal compounding unit 250 may perform temporal compounding on the sequence of reconstructed US images output from the reconstruction module 141. In another example, the temporal compounding unit 250 may perform temporal compounding on the sequence of US RF data and provide the resulting temporal compounding US RF data to the reconstruction module 141 to reconstruct a compounding image. As an example of temporal compounding, the sequence of frames may be averaged to achieve the compounding frame, and a weighted average may also be performed for the sequence of frames to achieve the compounding frame. The temporal compounding step 360 is an optional step. In an example, for 2D US imaging with high frame rate, temporal compounding may be used to enhance the needle in the US image. In another example, for 3D US imaging, temporal compounding may not be used to ensure an adequate frame rate for imaging if the frame rate is not high enough.

The location of the line feature as the needle determined at the false needle feature removing step 350 may be overlaid on an US image of a frame by the overlaying unit 260 (step 370) to produce an enhanced image, in which the location of the needle is enhanced. In an example, the overlaying unit 260 may overlay the location of the line feature as the needle on the compounding frame achieved at the temporal compounding step 360 to produce an enhanced image. In another example, the overlaying unit 260 may overlay the location of the line feature as the needle on an US image of one of the sequence of frames, for example, overlay the location of the line feature on the US image of the last frame of the sequence to produce an enhanced image. In an example, the overlaying unit 260 may highlight the locations of the line feature as the needle in the US image with recognizable intensity or color.

The enhanced image may be output to the display 150 to display to a viewer such as a clinician who is performing the insertion of the needle into the subject. With the improved needle visibility in the enhanced US image, it may help the clinician to place the needle at the desired location with less difficulty and more accuracy.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the system claims enumerating several units, several of these units can be embodied by one and the same item of software and/or hardware. The usage of the words first, second and third, et cetera, does not indicate any ordering. These words are to be interpreted as names.

The invention claimed is:

1. A method of needle visualization enhancement in ultrasound imaging, comprising acts of:
   performing by a processor a Radon transform (RT) on a sequence of frames to detect line features in the frames, a frame comprising ultrasound (US) radio-frequency (RF) data obtained during monitoring the insertion of a needle into a subject or an US image reconstructed from the RF data;
   removing by the processor line features which remain substantially stationary among the frames as false needles while locating a line feature which extends among the frames as the needle;
   overlaying by the processor the location of the line feature as the needle on an US image of a frame to produce an enhanced image to be displayed; and
   outputting an output signal by the processor for producing the enhanced image to be displayed,
   wherein said act of removing of line features which remain substantially stationary among the frames as false needles while locating a line feature which extends among the frames as the needle comprises acts of:
   for two consecutive frames of the sequence after the RT, determining the location difference of a detected line feature between the two consecutive frames, and accumulating the location differences of the line feature to obtain an accumulated location difference of the line feature; and
   removing a line feature as false needle if the accumulated location difference of the line feature is below a threshold, and locating a line feature as the needle if the accumulated location difference of the line feature is above the threshold.

2. The method according to claim 1, wherein said act of removing of line features which remain substantially stationary among the frames as false needles while locating a line feature which extends among the frames as the needle further comprising:
   comparing the locations of a detected line feature among the frames on a basis of one frame to another; and
   removing a line feature as a false needle if the location difference of the line feature among the frames is below a threshold, and locating a line feature as the needle if the location difference of the line feature among the frames is above the threshold.

3. The method according to claim 1, wherein, before the act of performing RT, the method further comprises acts of:
   calculating a global motion vector for each frame of the frames relative to a reference frame; and
   performing motion compensation for each frame of the frames, using its global motion vector.

4. The method according to claim 1, wherein before the act of performing RT, the method further comprises an act of binarized the frames are into dark and bright frames by thresholding.

5. The method according to claim 1, further comprising acts of:
   performing temporal compounding on the sequence of frames to produce a compounding frame; and
   overlaying the location of the line feature as the needle on the US image of the compounding frame to produce the enhanced image.

6. The method of claim 1, further comprising an act of displaying the enhanced image on a display.

7. An apparatus for needle visualization enhancement in ultrasound imaging, comprising:
   a Radon transform (RT) unit configured to perform RT on a sequence of frames to detect line features in the frames, a frame comprising ultrasound (US) radio-frequency (RF) data obtained during monitoring the insertion of a needle into a subject or an US image reconstructed from the RF data;
   a false needle feature removing unit configured to remove line features which remain substantially stationary among the frames as false needles while locating a line feature which extends among the frames as the needle;
   an overlaying unit configured to overlay the location of the line feature as the needle on an US image of a frame to produce an enhanced image to be displayed; and
   a display configured to display the enhanced image,
   wherein the false needle feature removing unit is further configured to
   determine, for two consecutive frames of the sequence after the RT, the location difference of a detected line feature between the two consecutive frames, and accumulate the location differences of the line feature to obtain an accumulated location difference of the line feature; and
   remove a line feature as false needle if the accumulated location difference of the line feature is below a threshold, and locate a line feature as the needle if the accumulated location difference of the line feature is above the threshold.

8. The apparatus according to claim 7, wherein the false needle feature removing unit is further configured to
   compare the locations of a detected line feature among the frames on a basis of one frame to another; and
   remove a line feature as false needle if the location difference of the line feature among the frames is below a threshold, and locate a line feature as the needle if the location difference of the line feature among the frames is above the threshold.

9. The apparatus according to claim 7, further comprising a motion compensation unit configured to
   calculate a global motion vector for each frame of the frames relative to a reference frame; and
   perform motion compensation for each frame of the frames, using its global motion vector.

10. The apparatus according to claim 7, further comprising a temporal compounding unit configured to perform temporal compounding on the sequence of frames to produce a compounding frame,
    wherein the overlaying unit is configured to overlay the location of the line feature as the needle on the US image of the compounding frame to produce the enhanced image.

11. An ultrasound imaging system comprising
    an ultrasound transducer array configured to pick up ultrasound (US) radio-frequency (RF) signals;
    an image processor configured to perform a Radon transform (RT) on a sequence of frames to detect line features in the frames, a frame comprising US radio-frequency (RF) data obtained during monitoring the insertion of a needle into a subject or an US image reconstructed from the RF data, and remove line features which remain substantially stationary among the frames as false needles while locating a line feature which extends among the frames as the needle, and overlay the location of the line feature as the needle on an US image of a frame to produce an enhanced image to be displayed; and
    a display configured to display the enhanced image, wherein the image processor is further configured to
determine, for two consecutive frames of the sequence after the RT, the location difference of a detected line feature between the two consecutive frames, and accumulate the location differences of the line feature to obtain an accumulated location difference of the line feature; and
remove a line feature as false needle if the accumulated location difference of the line feature is below a threshold, and locate a line feature as the needle if the accumulated location difference of the line feature is above the threshold.

12. The system according to claim 11, wherein the image processor is further configured to
compare the locations of a detected line feature among the frames on a basis of one frame to another; and
remove a line feature as false needle if the location difference of the line feature among the frames is below a threshold, and locate a line feature as the needle if the location difference of the line feature among the frames is above the threshold.

13. The system according to claim 11, wherein, before performing RT, the image processor is further configured to
calculate a global motion vector for each frame of the frames relative to a reference frame; and
perform motion compensation for each frame of the frames using its global motion vector.

* * * * *